United States Patent [19]

Sasaki et al.

[11] Patent Number: 5,121,634
[45] Date of Patent: Jun. 16, 1992

[54] ULTRASONIC MICROSCOPE

[75] Inventors: Yasuo Sasaki; Mitsugu Sakai; Yasuhiro Omura; Koichi Karaki, all of Tokyo, Japan

[73] Assignee: Olympus Optical Co., Ltd., Tokyo, Japan

[21] Appl. No.: 626,372

[22] Filed: Dec. 5, 1990

Related U.S. Application Data

[62] Division of Ser. No. 399,318, Aug. 28, 1989, abandoned.

[30] Foreign Application Priority Data

Sep. 1, 1988 [JP] Japan ................................ 63-216340

[51] Int. Cl.⁵ .................... G01N 29/06; G01N 29/26
[52] U.S. Cl. ............................................ 73/606; 73/620
[58] Field of Search .................... 73/606, 620, 627, 629

[56] References Cited

U.S. PATENT DOCUMENTS

| | | | |
|---|---|---|---|
| 4,028,933 | 6/1977 | Lemons et al. | 73/627 |
| 4,541,281 | 9/1985 | Chubachi et al. | 73/606 |
| 4,655,083 | 4/1987 | Chubachi | 73/606 |
| 4,683,751 | 8/1987 | Imade et al. | 73/606 |
| 4,920,803 | 5/1990 | Karaki et al. | 73/606 |
| 4,977,544 | 12/1990 | Karaki et al. | 73/620 |
| 4,977,779 | 12/1990 | Karaki et al. | 73/620 |

FOREIGN PATENT DOCUMENTS

58-196453 11/1983 Japan .
59-44582 10/1984 Japan .
62-249052 10/1987 Japan .

Primary Examiner—Hezron E. Williams
Assistant Examiner—Rose M. Finley
Attorney, Agent, or Firm—Frishauf, Holtz, Goodman & Woodward

[57] ABSTRACT

An ultrasonic microscope comprises an acoustic lens for emitting an ultrasonic beam, a movable shaft for supporting a sample, and a drive circuit for moving the movable shaft and thus the sample relative to the acoustic lens in a z-direction. Two signals for eliminating x-direction and y-direction inclinations of the sample relative to the acoustic lens are supplied to the drive circuit in synchronism with an x-direction drive signal and a y-direction drive signal, so that the sample is moved in the z-direction and scanned with the ultrasonic beam in an x-y direction while the sample inclination sample to the acoustic lens is being eliminated.

4 Claims, 6 Drawing Sheets

ULTRASONIC MICROSCOPE

This application is a division of U.S. application Ser. No. 07/399,318, filed Aug. 28, 1989 now abandoned.

BACKGROUND OF THE INVENTION

1. Field of the Invention

The present invention relates to an ultrasonic microscope.

2. Description of the Related Art

An ultrasonic microscope is known in which a sample is two-dimensionally scanned with an ultrasonic beam, and the waves passing through, or reflected from, the sample are processed to form an image of the sample. Ultrasonic microscopes of this type are disclosed in various publications, such as Published Examined Japanese Patent Application No. 59-44582 and Published Unexamined Japanese Patent Application No. 58-196453.

In these microscopes, that surface of a sample which is to be scanned with an ultrasonic beam must be substantially parallel to the focal plane of the acoustic lens which focuses the beam onto that surface of the sample, in order to form a clear image of the sample. Published Unexamined Japanese Patent Application No. 62-249052 discloses an ultrasonic microscope which can be so adjusted that the scanning surface of the sample is substantially parallel with the focal plane of the acoustic lens. This microscope includes a vibrator and a goniometer. The vibrator can vibrate the acoustic lens in one direction. The goniometer is used to support a sample, and has a mechanism for adjusting the inclination of the sample in both an x-direction and a y-direction. Either the vibrator or the goniometer is rotated in the x-y plane, thereby changing the direction in which the acoustic lens vibrates. The inclination-adjusting mechanism is operated to distribute the intensities of the ultrasonic beams reflected from the sample, uniformly in the direction in which the acoustic lens vibrates. When the intensities of the ultrasonic beams are distributed uniformly in this direction, the scanning surface of the sample and the focal plane of the acoustic lens are substantially parallel to each other.

The ultrasonic microscope disclosed in Published Unexamined Japanese Patent Application No. 62-249052 is complex, not only because the goniometer has a mechanism for adjusting the inclination of the sample in both the x-direction and the y-direction, but also because the goniometer or the vibrator for vibrating the acoustic lens is rotated in the x-y plane in order to adjust the inclination of the scanning surface of the sample. Further, it is time-consuming to successfully adjust the inclination of the scanning surface of the sample. There is another problem with this ultrasonic microscope. When cryogenic liquid, such as liquid nitrogen, liquid argon, or liquid helium, is filled in the gap between the acoustic lens and the sample and used as a medium for transmitting the ultrasonic beam, it is necessary to locate both the acoustic lens and the goniometer within an adiabatic vessel. This makes it even more difficult to adjust the inclination of the scanning surface of the sample.

SUMMARY OF THE INVENTION

Accordingly, the object of the present invention is to provide an ultrasonic microscope which has a simple structure, and in which the inclination of the scanning surface of a sample to the focal plane of the acoustic lens can be easily and correctly adjusted even if a cryogenic liquid is used as a medium for transmitting an ultrasonic beam.

DETAILED DESCRIPTION OF THE PREFERRED EMBODIMENTS

An ultrasonic microscope, which is an embodiment of the invention, will now be described with reference to FIG. 1. As is shown in this figure, the microscope comprises a frame 5 made of nonmagnetic material, an upper yoke 10 fixed in the upper portion of the frame 5, and a lower yoke 11 fixed in the middle portion of the frame 5.

The upper yoke 10 has three arms extending downward, parallel to one another. A permanent magnet 12 is embedded in the proximal portion of the center arm. The lower yoke 11 also has three arms extending upward, parallel to one another. The central arm of the lower yoke 11 has a vertical guide hole 13 extending through the lower yoke 11. A hollow cylindrical permanent magnet 14 is embedded in the lower yoke 11 and is located coaxial with the guide hole 13.

A movable shaft 4 is located vertically within the frame 5. The shaft 4 is supported by two leaf springs 6 and 7 connected to the inner side of the frame 5, and can move up and down. The shaft 4 comprises a hollow cylindrical upper portion 4a, an intermediate portion, and a thin lower portion.

The center arm of the upper yoke 10 is loosely inserted in the upper portion 4a of the movable shaft 4. An upper coil 8 is wound around the upper portion 4a of the shaft 4. The coil 8 is electrically connected to a drive circuit 20 located outside the frame 5 and having a DC power source. When a current is supplied to the upper coil 8 from the drive circuit 20, the coil 8 generates a magnetic field. This magnetic field cooperates with the magnetic field of the permanent magnet 12, to move the shaft 4 up or down against the bias of the leaf springs 6 and 7, for a distance proportional to the amount of the current flowing through the upper coil 8.

The lower portion of the movable shaft 4 extends via the vertical guide hole 13 into the lower portion of the frame 5. A sample 3 is attached to the tip of this lower end portion. A hollow cylinder 4b is coaxially secured to the intermediate portion of the movable shaft 4, and surrounds the center arm of the lower yoke 11, which in turn surrounds the lower end portion of the shaft 4. A lower coil 9 is wound around the cylinder 4b. The lower coil 9 cooperates with the magnetic field of the permanent magnet 14, to generate an electrical current when the shaft 4 moves up or down. This current is proportional to the speed at which the shaft 4 moves. The lower coil 9 is connected to the input of the drive circuit 20. Therefore, the current generated by the lower coil 9 is supplied to the drive circuit 20. As a result of this, the drive circuit 20 controls the current supplied to the upper coil 8 in accordance with the current the coil 9 has generated, thereby to stop the movable shaft 4. In other words, the lower coil 9 locks the shaft 4 at the position to which the shaft 4 has been moved by means of the upper coil 8.

The lower portion of the frame 5 contains an acoustic lens 1. The acoustic lens 1 is attached to the upper end of an x-y scanner 2 which is secured to the bottom of the frame 5. The x-y scanner 2 is so positioned such that the lens 1 is spaced apart from the sample 3 by a predetermined distance. The x-y scanner 2 can move in a horizontal plane, in an x-direction and in a y-direction. Hence, the acoustic lens 1 can also move in a horizontal plane, thereby to scan the sample 3 with the ultrasonic beam.

Figure 1:
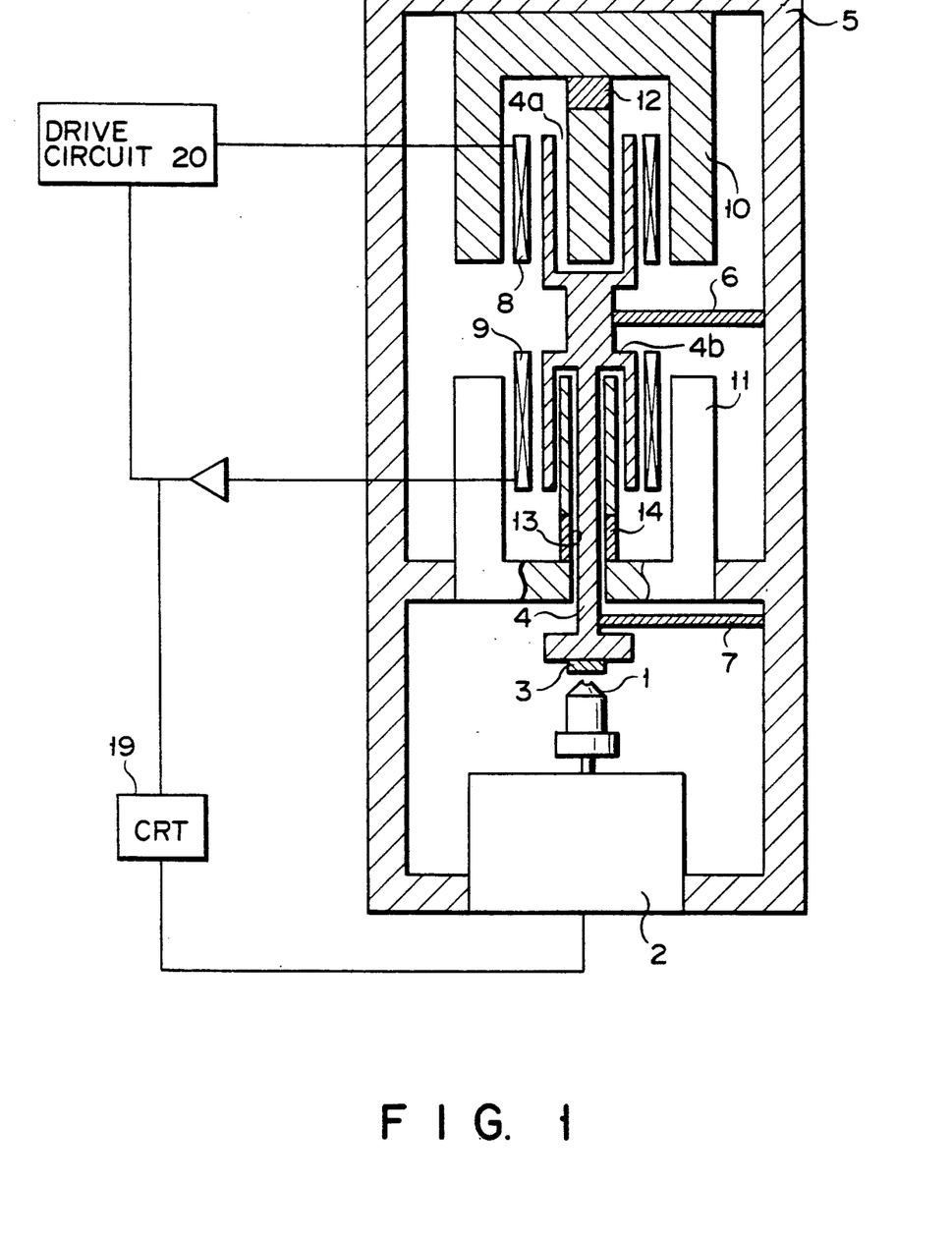
FIG. 1 is a sectional view illustrating an ultrasonic microscope according to the present invention.
Figure 2:
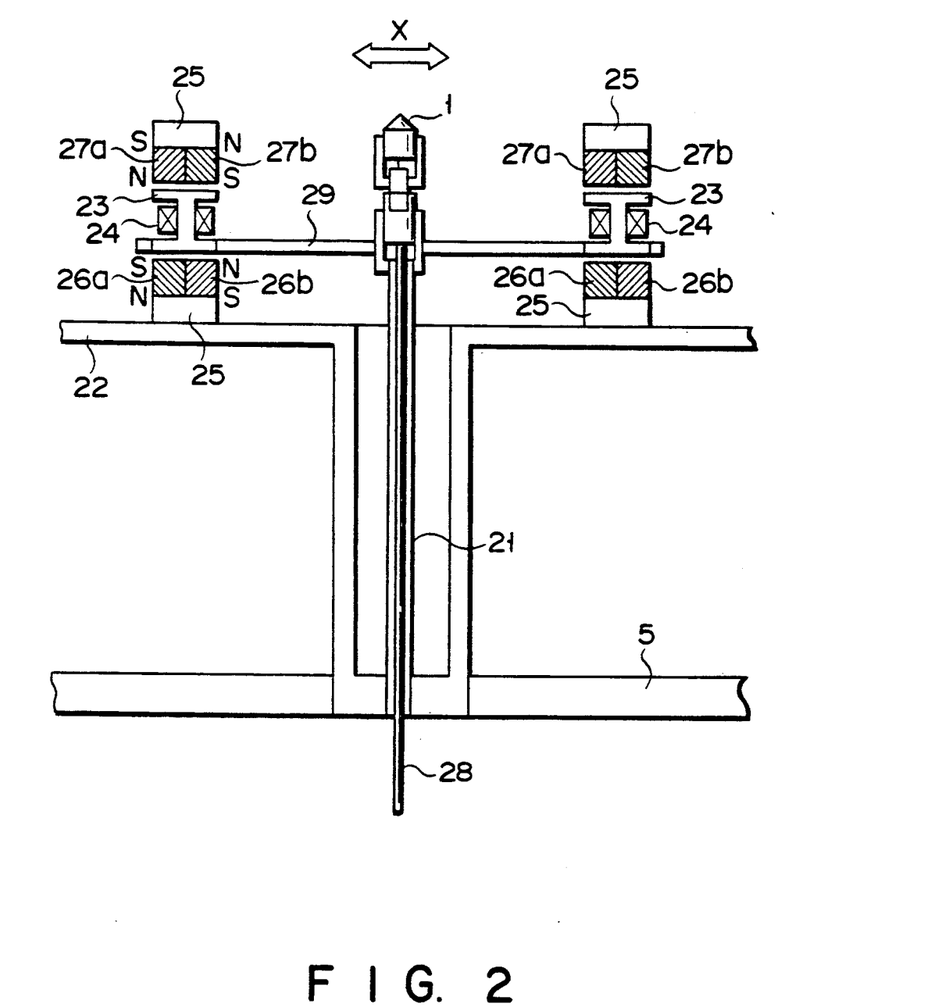
FIG. 2 is also a sectional view showing the x-y scanner incorporated in the ultrasonic microscope shown in FIG. 1.

FIG. 2 illustrates the x-y scanner 2 incorporated in the ultrasonic microscope shown in FIG. 1. As is shown in this figure, the acoustic lens 1, which is made of nonmagnetic material, is mounted on the center of a cross-shaped movable member 29 having four arms spaced apart at angular intervals of 90°. The member 29 is supported on a base 22 by means of a hollow flexible pillar 21, and can move in the x-direction and in the y-direction. The pillar 21 is made of, for example, stainless steel. Four bobbins 23 made of nonmagnetic material such as aluminum are connected to the free ends of the arms of the member 29, respectively. Since the arms of the member 29 have the same length, the bobbins 23 are located symmetrically with respect to the acoustic lens 1, in both the x-direction and the y-direction. (Only two bobbins 23 connected to the arms extending in the x-direction are illustrated in FIG. 2). A length of enamel-coated copper wire is wound around each of the bobbins 23, thus forming a coil 24. Four yokes 25, shaped like a square frame or a U-shaped frame, are mounted on the base 22 and straddle the four coils 24, respectively. Two permanent magnets 26a and 26b are fastened to the lower arm of each yoke 25, and two permanent magnets 27a and 27b are fastened to the upper arm of each yoke 25. These permanent magnets 26a, 26b, 27a, and 27b are positioned such that the magnetic fluxes, which they generate and which extend in opposite directions, pass through each coil 24.

Thus, in the present embodiment, when a required current is applied to one of coils 24 in each pair, it is combined with the magnetic fluxes of permanent magnets 26a, 26b, 27a and 27b to make an electromagnetic action. This action causes movable member 29 to drive acoustic lens 1 two-dimensionally in the x- and y-directions. In this manner, sample 3 is two-dimensionally scanned with an ultrasonic beam emitted from lens 1, and the region for scanning, i.e., the field of view, is selected. When the other of coils 24 in each pair is moved, a current is caused to flow through it by an electromotive force. By detecting this current, therefore, the moving speed of acoustic lens 1 may be monitored. Coaxial cable 28, which is connected to lens 1, is passed through flexible pillar 21, led to the outside of the frame 5, and connected to a signal processing circuit. The lead wire of each coil 24 is also led to the outside of the frame 5, and connected to a drive circuit 20.

Figure 3:
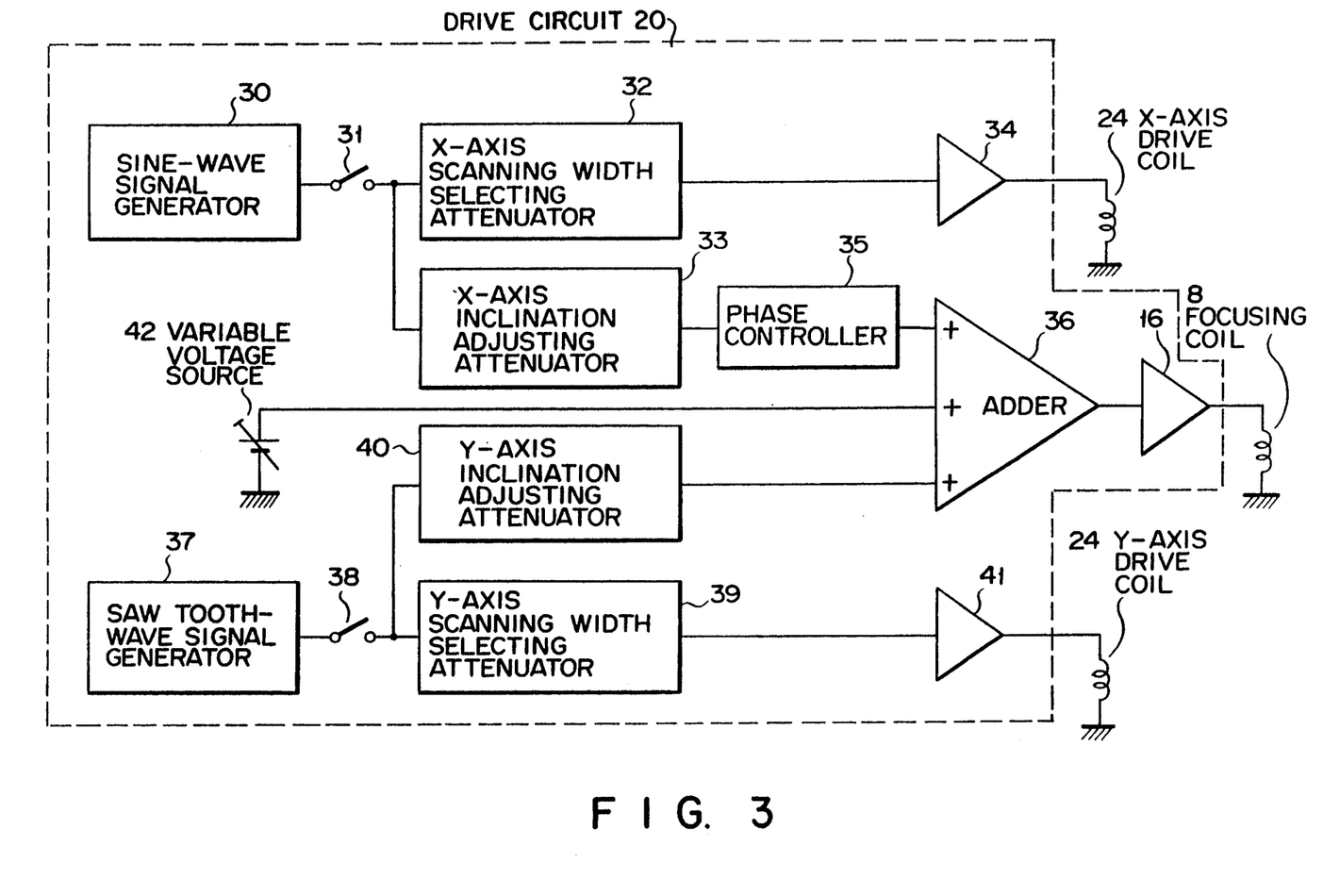
FIG. 3 is a diagram illustrating the drive circuit used in the microscope for driving the shaft and the acoustic lens, both incorporated in the ultrasonic microscope.

FIG. 3 is a diagram schematically showing the drive circuit 20. As this figure illustrates, the sinewave signal output by a sine-wave signal generator 30 is supplied via a switch 31 to an attenuator 32 for selecting an x-axis scanning width. The signal output by this attenuator 32 is amplified by a power amplifier 34 and is then supplied to the coil 24, which is used for moving the acoustic lens 1 in the x-direction. The sine-wave signal is also supplied via the switch 31 to an attenuator 33 for adjusting the x-axis inclination of the movable member 29. The signal output by the attenuator 33 has its phase adjusted by a phase controller 35 and is then supplied to an adder 36.

Meanwhile, the sawtooth-wave signal output by a sawtooth-wave signal generator 37 is supplied via a switch 38 to an attenuator 39 for selecting a y-axis scanning width. The signal output by this attenuator 39 is amplified by a power amplifier 41 and is then supplied to the coil 24 which is used for moving the acoustic lens 1 in the y-direction. The sawtooth-wave signal is also supplied through the switch 38 to an attenuator 40 for adjusting the y-axis inclination of the movable member 29. The signal output by the attenuator 40 is supplied to the adder 36.

A variable voltage source 42 is connected to the adder 36 to supply the adder 36 with a focusing offset signal for moving the sample 3 to a position where the scanning surface thereof is in the focal plane of the acoustic lens 1. The signal output by the adder 36, which is the sum of the focusing offset signal and the signal output by the phase controller 35 and the attenuator 40, is supplied, as a focusing signal, to the upper coil 8 through a power amplifier 16. In accordance with this focusing signal, the upper coil 8 generates a magnetic field, which cooperates with the magnetic field of the permanent magnet 12, to move the shaft 4 in a z-direction, that is, up or down, against the bias of the leaf springs 6 and 7.

Figure 4:
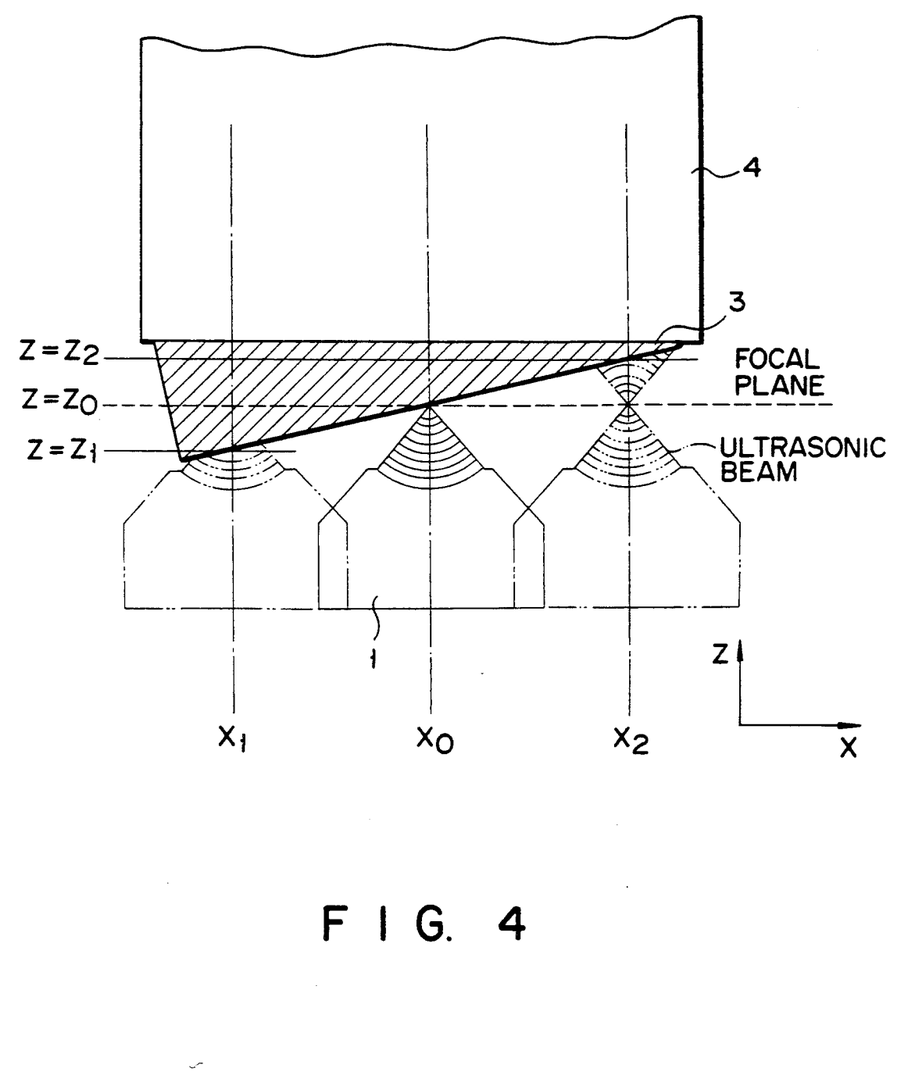
FIG. 4 is a diagram explaining the operation of the ultrasonic microscope shown in FIG. 1.

FIG. 4 is a diagram representing the positional relationship which the acoustic lens 1 and the sample 3 have when the scanning surface of the sample 3 is inclined to the focal plane of the acoustic lens 1. As is shown in this figure, the focal point of the lens 1 moves between positions x1 and x2 as the acoustic lens 1 is moved to scan the sample 3 in the x-direction. The focal point can be on the scanning surface of the sample 3 when it is moved to the intermediate position x0 which is exactly half way between the positions x1 and x2. As is shown in FIG. 4, the scanning surface of the sample 3 is moved between positions z1 and z2 as the shaft 4 is moved in the z-direction. The focal point of the lens 1, which is located at position x0, is on the scanning surface when this surface is located at the intermediate position z0 which is exactly half way between the positions z1 and z2. The focal plane of lens 1 is parallel to the x-y plane given by the position z0.

Figure 5:
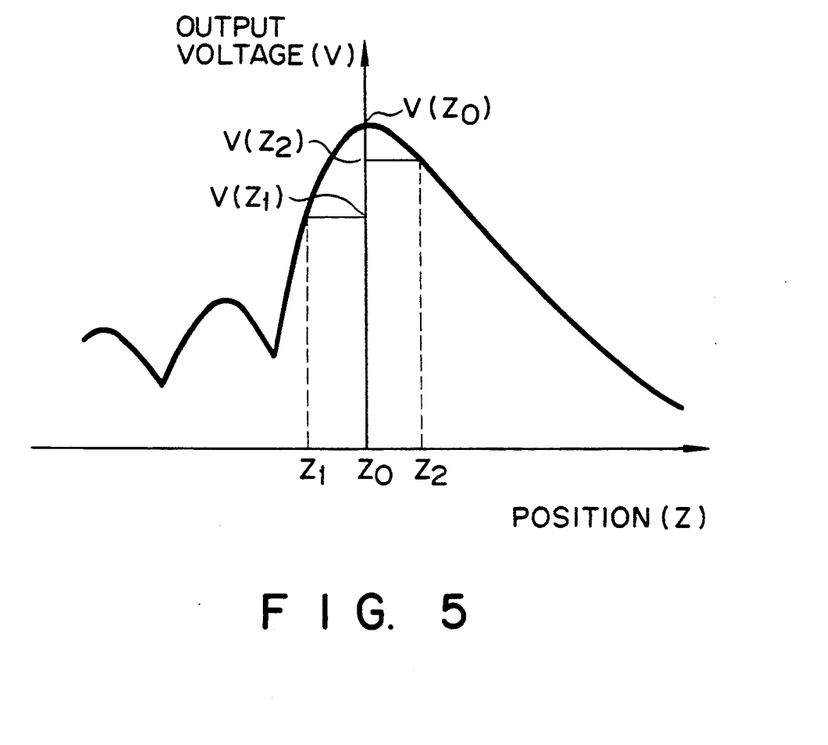
FIG. 5 is a graph illustrating the relationship between the distance between a sample and the acoustic lens used in the microscope, and the voltage equivalent to the intensity of an ultrasonic beam reflected from the sample.

The operation of the ultrasonic microscope, described above, will now be described with reference to FIGS. 4, 5, and 6 and also FIGS. 7A to 7C.

First, the acoustic lens 1 emits an ultrasonic beam to the sample 3. This beam is reflected from the scanning surface of the sample 3. The lens 1 receives the reflected beam and converts this beam into an electrical signal whose voltage is proportional to the intensity of the reflected beam. The voltage V of the signal has a specific relationship with the distance between the focal point of the lens 1 and the scanning surface of the sample 3, which depends on the material of the sample 3 and is represented by a so-called V(z) curve shown in FIG. 5. In FIG. 5, the positions which the focal point of the lens 1 can take with respect to the sample 3 are plotted on the X axis, whereas the voltage V of the signal is plotted on the Y axis, As is evident from FIG. 5, the voltage V is maximum, at value V(z0), when the scanning surface of the sample 3 is located at the position z0. Also, as is clearly understood from FIG. 5, the voltage has value V(z1) when the scanning surface is located at the position z1, and value (z2) which is greater than the value V(z1), when the scanning surface is located at the position z2.

Figure 6:
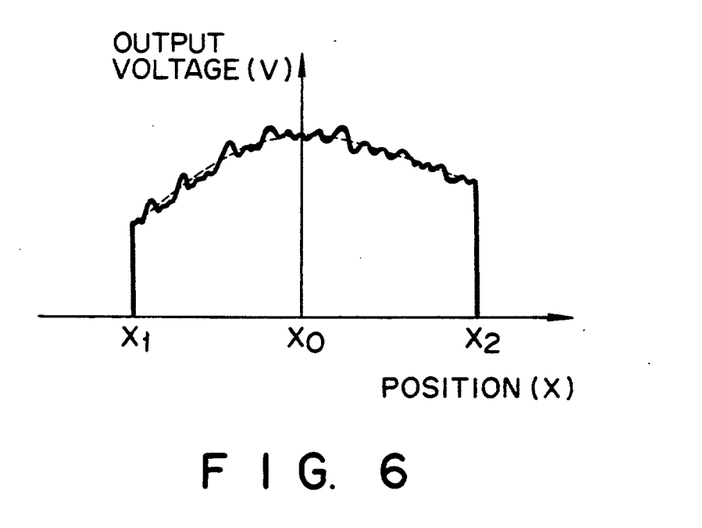
FIG. 6 is a graph showing the relationship between the voltage output by the acoustic lens and the position of the lens in the x-direction.
Figure 7A:
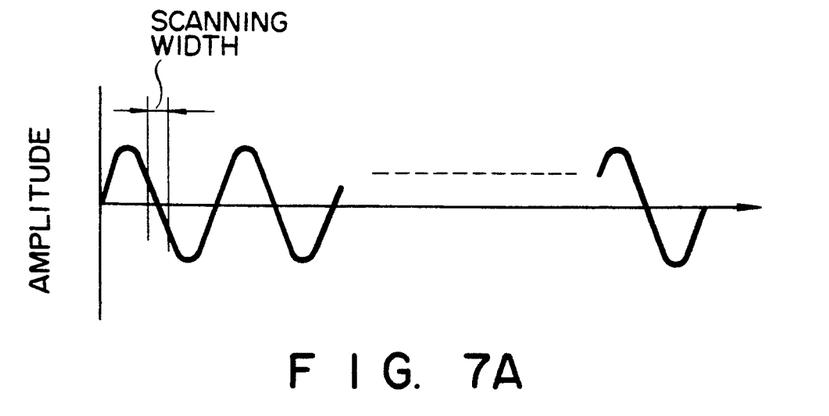
FIGS. 7A to 7C show various electrical signals used in the ultrasonic microscope illustrated in FIG. 1.
Figure 7B:
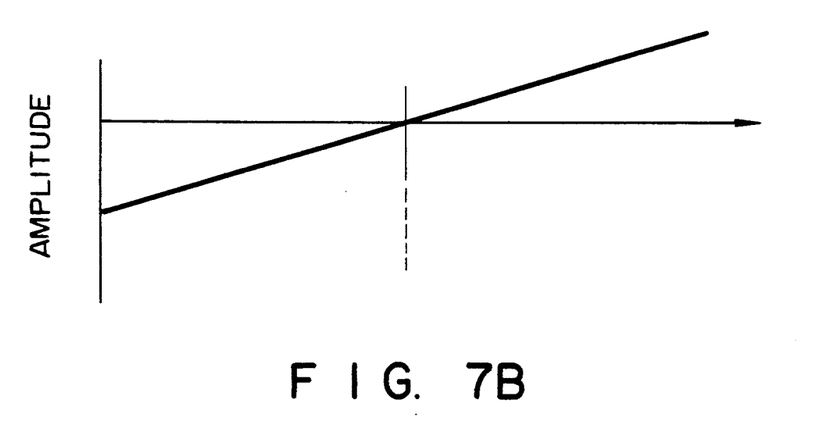

The output voltage V of the signal output by the lens 1 varies as the sample 3 is scanned in the x-direction, as is illustrated in FIG. 6. As is evident from FIG. 6, the voltage V has the maximum value when the focal point of the acoustic lens 1 is located at position x0. Theoretically, as the broken-line curve shows, the voltage V gradually increases as the focal point moves from position x1 to the position x0, and gradually decreases as the focal point moves from position x0 to the position x2. Practically, however, the voltage V varies in such a complex manner as is indicated by the solid-line curve, since the scanning surface of the sample 3 has depressions and protrusions.

As has been described, when the scanning surface of the sample 3 is inclined to the focal plane of the acoustic lens 1, and the acoustic lens 1 is moved in the x-y plane, thus scanning the sample 3 with the ultrasonic beam, the voltage output by the lens 1 varies linearly at a slope which is proportional to the angle of inclination of the scanning surface of the sample 3.

When the switches 31 and 38 are turned on and off, respectively, the shaft 4 and, thus, the sample 3 are moved in the z-direction, and the acoustic lens 1 emits the ultrasonic beam to the sample 3 and receives the beam reflected therefrom, while being moved in the x-direction. In this condition, the operator operates the attenuator 32, adjusting the amplitude of the sinewave signal (FIG. 7A) output by the sine-wave signal generator 30 and being supplied to the x-axis drive coil 24, such that the scanning width in the x-direction has a desired value. At the same time, the voltage which the lens 1 generates from the ultrasonic beam reflected from the sample 3 is monitored by means of a CRT 19. Looking at the slope at which this voltage is varying, the operator operates the attenuator 33 and the phase controller 35, thereby adjusting the amplitude and phase of the sine-wave signal being applied to the focusing coil 8.

Then, the switches 31 and 38 are turned off and on, respectively, whereby the acoustic lens 1 and the sample 3 are moved in the y-direction and the z-direction, respectively, while the lens 1 keeps emitting an ultrasonic beam to the sample 3 and receiving the beam reflected therefrom. In this condition, the operator operates the attenuator 39, adjusting the amplitude of the sawtooth-wave signal (FIG. 7B) output by the sawtooth-wave generator 37 and supplied to the y-axis drive coil 24, such that the scanning width in the y-direction has a desired value. Also, looking at the slope at which the voltage, being generated by the lens 1 from the beam reflected from the sample 3, is varying, the operator operates the attenuator 40, thereby adjusting the amplitude of the sawtooth-wave signal being applied to the focusing coil 8.

After signals have been generated which will eliminate the inclination of the sample 3 relative to the focal plane of the lens 1, in both the x-direction and the y-direction, the operator turns on both switches 31 and 38, thereby to form an ultrasonic image of the sample 3.

Figure 7C:
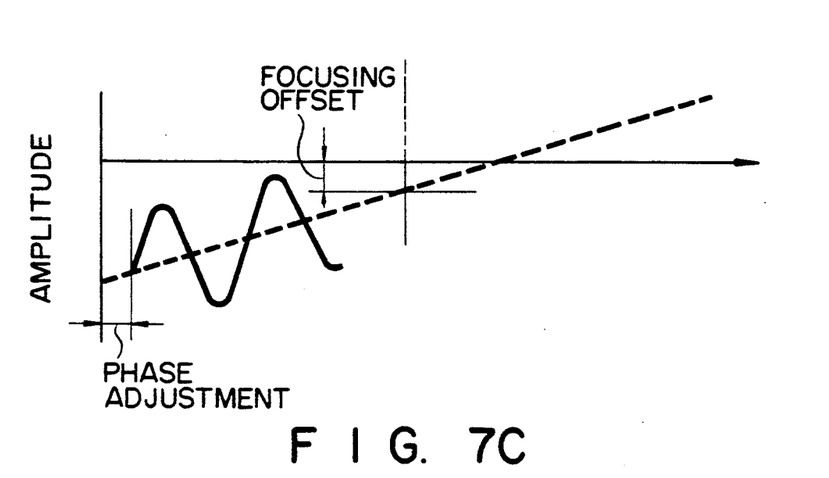

Hence, the focus-offset signal shown in FIG. 7C is supplied to the focusing coil 8. As can be understood from FIG. 7C, the focus-offset signal is a combination of the signals for eliminating the x-direction inclination of the sample 3 and the y-direction inclination thereof. In accordance with the focus-offset signal, the focusing coil 8 moves the sample 3 in the z-direction such that the inclination of the scanning surface of the sample 3 to the focal plane of the acoustic lens 1 is eliminated, while the sample 3 is being scanned with the ultrasonic beam emitted from the lens 1. As a result, a high-quality ultrasonic image of the sample 3 can be obtained.

The present invention is not limited to the embodiment described above. Various changes and modifications can be made, without departing from the scope of the invention. For example, the operator can operate the attenuators 33 and 40, thereby to eliminate the x-direction and y-direction inclinations of the sample 3, in accordance with the ultrasonic image of the sample 3 displayed by the CRT 19 while the acoustic lens 1 is scanning the sample 3 in both the x-direction and the y-direction. Alternatively, both attenuators 33 and 40 can be automatically operated for the same purpose, in accordance with the voltage which the acoustic lens 1 generates from the ultrasonic beam reflected from the sample 1. Further, the acoustic lens 1 can be fixed in place, whereas the shaft 4 can be moved not only in the z-direction but also in the x-direction and the y-direction, so that the sample 3 supported on the tip of the shaft 4 is scanned in the x-direction and the y-direction. Still further, the lens 1 can be moved in the z-direction only, whereas the shaft 4 is moved in the x-direction and the y-direction, so that the sample 3 is scanned in the x-direction and the y-direction. Moreover, the section shown in FIG. 1 can be immersed in a bath of cryogenic liquid when the cryogenic liquid is used as beam-transmission medium.

As has been described, the present invention provides an ultrasonic microscope comprising z-direction drive means for moving the acoustic lens and means supporting the sample relative to each other, in the z-direction. Two signals for eliminating the x-direction and the y-direction inclinations of the sample 3 relative to the acoustic lens are supplied to the z-direction drive means, in synchronism with an x-direction drive signal and a y-direction drive signal, thereby moving the lens and the sample relative to each other in the z-direction. Hence, the sample is scanned while its inclination to the acoustic lens is being eliminated. The inclination is eliminated more easily than by mechanical means, such as a goniometer, which is used in the conventional ultrasonic microscope. Not requiring such mechanical means, the microscope of the present invention is simple in structure. In addition, the ultrasonic microscope according to the invention can be applied to the type wherein cryogenic liquid is used as the beam-transmission medium.

What is claimed is:

1. A method of scanning a sample in an ultrasonic microscope, comprising steps of:

supporting and positioning a sample by a sample-supporting means so that the sample is in a face-to-face relation with an acoustic lens;

emitting an ultrasonic beam from the acoustic lens onto the sample;

moving said acoustic lens and said sample-supporting means relative to each other in a Z-direction by a Z-direction drive means, thereby changing the distance between said acoustic lens and said sample;

moving said acoustic lens and said sample-supporting means relative to each other in an X-direction and in a Y-direction in an X-Y plane perpendicular to the Z-direction by X-and Y-direction drive means, thereby scanning said sample with the ultrasonic beam;

supplying an X-direction drive signal and a Y-direction drive signal respectively to said X-and Y-direction drive means by signal-generating means, thereby moving at least one of said acoustic lens and said sample relative to each other in said X-Y plane to scan said sample with the ultrasonic beam;

supplying an X-direction inclination-eliminating signal and a Y-direction inclination-eliminating signal to said Z-direction drive means, said X- and Y-direction inclination-eliminating signals being supplied at the same time as said X- and Y-direction signals are supplied to their respective X- and Y-direction drive means, and respectively in synchronism with the X-direction drive signal and the Y-direction drive signal, thereby moving said acoustic lens and said sample-supporting means relative to each other in the Z-direction, so that said sample is scanned while an inclination of a scanned surface of said sample is being eliminated; and adjusting an amplitude and phase of said X-direction inclination-eliminating signal supplied to said Z-direction drive means.

2. The method of claim 1, further comprising controlling the supplying of the Y-direction inclination-eliminating signal to said Z-direction drive means.

3. The method of claim 2, further comprising:

adding the signal generated by said adjusting step and the signal generated by said controlling step by means of an adder, and generating an added signal; and supplying said added signal to said Z-direction drive means.

4. The method of claim 3, further comprising supplying a focus-offset signal from a variable voltage source to said adder for moving said sample to a position where a scanned surface of said sample is in a focal plane of said acoustic lens.

* * * * *